United States Patent
Schuck et al.

(10) Patent No.: US 12,080,422 B1
(45) Date of Patent: *Sep. 3, 2024

(54) PATIENT IDENTIFICATION USING PASSIVE SENSORS

(71) Applicant: TeleTracking Technologies, Inc., Pittsburgh, PA (US)

(72) Inventors: Joseph Christopher Schuck, Pittsburgh, PA (US); Raghen Nicole Morrow, Pittsburgh, PA (US)

(73) Assignee: TELETRACKING TECHNOLOGIES, INC., Pittsburgh, PA (US)

( * ) Notice: Subject to any disclaimer, the term of this patent is extended or adjusted under 35 U.S.C. 154(b) by 50 days.

This patent is subject to a terminal disclaimer.

(21) Appl. No.: 17/748,953

(22) Filed: May 19, 2022

Related U.S. Application Data

(63) Continuation of application No. 15/859,609, filed on Dec. 31, 2017, now Pat. No. 11,342,074.

(51) Int. Cl.
  *G16H 40/67* (2018.01)
  *G16H 40/20* (2018.01)

(52) U.S. Cl.
  CPC ............. *G16H 40/67* (2018.01); *G16H 40/20* (2018.01)

(58) Field of Classification Search
  CPC ................................ G16H 40/67; G16H 40/20
  USPC ........................................................... 705/2
  See application file for complete search history.

(56) References Cited

U.S. PATENT DOCUMENTS

| | | | |
|---|---|---|---|
| 8,799,011 B2 * | 8/2014 | Wilson | A61B 5/002 |
| | | | 705/2 |
| 10,243,255 B2 * | 3/2019 | Rokhsaz | H01Q 5/335 |
| 10,319,476 B1 * | 6/2019 | LaBorde | G06N 3/08 |
| 10,770,182 B2 * | 9/2020 | Sherwood | A61B 5/082 |
| 11,342,074 B1 * | 5/2022 | Schuck | G16H 40/20 |
| 2003/0050794 A1 * | 3/2003 | Keck | G16H 40/20 |
| | | | 705/2 |
| 2004/0030531 A1 | 2/2004 | Miller et al. | |
| 2004/0143458 A1 | 7/2004 | Pulkkinen et al. | |
| 2005/0124864 A1 | 6/2005 | Mack et al. | |
| 2006/0010007 A1 | 1/2006 | Denman et al. | |
| 2006/0288095 A1 | 12/2006 | Torok et al. | |

(Continued)

*Primary Examiner* — Peter H Choi
*Assistant Examiner* — Rachael Sojin Stone
(74) *Attorney, Agent, or Firm* — FERENCE & ASSOCIATES LLC

(57) ABSTRACT

One embodiment provides a method, including: receiving, at a passive sensor of a wearable identification device associated with a patient within a healthcare enterprise from a receiver of a patient status system and corresponding to a predetermined location within the healthcare enterprise, a request signal when the wearable identification device is detected at the predetermined location; deriving power for the passive sensor from the request signal and not from power circuitry within the wearable device; generating, at the passive sensor using the derived power, a transmission from the request signal, wherein the transmission includes identifying information associated with the wristband; and transmitting, from the passive sensor, the transmission to the receiver, wherein the transmission is utilized to update a status of the patient within the patient status system based upon detection of the passive sensor at the predetermined location. Other aspects are described and claimed.

20 Claims, 2 Drawing Sheets

(56) References Cited

U.S. PATENT DOCUMENTS

| | | |
|---|---|---|
| 2010/0036209 A1 | 2/2010 | Ferren et al. |
| 2015/0094914 A1* | 4/2015 | Abreu ................ B60H 1/00742 |
| | | 701/1 |
| 2015/0302538 A1* | 10/2015 | Mazar ................ G08B 21/0211 |
| | | 705/2 |
| 2016/0310077 A1 | 10/2016 | Hunter et al. |
| 2017/0132396 A1 | 5/2017 | Bechtold et al. |
| 2018/0122202 A1 | 5/2018 | Brantley |
| 2023/0352156 A1* | 11/2023 | Postrel ................ A61B 5/7405 |

* cited by examiner

PATIENT IDENTIFICATION USING PASSIVE SENSORS

CROSS REFERENCE TO RELATED APPLICATIONS

This application claims priority to U.S. patent application Ser. No. 15/859,609, filed Dec. 21, 2017, titled "Patient Identification Using Passive Sensors," the contents of which are incorporated by reference herein.

BACKGROUND

Healthcare enterprises may include different facilities for treating and caring for patients. These different facilities may be located either within a single building or located within different buildings. For example, a healthcare enterprise may have an emergency department located at one geographical location within a building and may also have a long-term care facility located at a different geographical location within a different building. In either case, the healthcare enterprise identifies the location of the patient within not only a single facility but across the entire enterprise system. Accordingly, when a patient is admitted to one or more of the healthcare enterprise facilities, the patient is usually outfitted with an identification object (e.g., wristband, identification badge, identification nametag, etc.). In some cases, the identification object may include one or more sensors that can be used by staff or systems of the healthcare enterprise to identify the location of a patient, or object, within the enterprise.

BRIEF SUMMARY

In summary, one aspect provides a method including: receiving, at a passive sensor of a wearable identification device associated with a patient within a healthcare enterprise from a receiver of a patient status system and corresponding to a predetermined location within the healthcare enterprise, a request signal when the wearable identification device is detected at the predetermined location; deriving power for the passive sensor from the request signal and not from power circuitry within the wearable device; generating, at the passive sensor using the derived power, a transmission from the request signal, wherein the transmission includes identifying information associated with the wristband; and transmitting, from the passive sensor, the transmission to the receiver, wherein the transmission is utilized to update a status of the patient within the patient status system based upon detection of the passive sensor at the predetermined location.

Another aspect provides an information handling device, including: a processor; a memory device that stores instructions that, when executed by the processor, causes the information handling device to: receive, at a passive sensor of a wearable identification device associated with a patient within a healthcare enterprise from a receiver of a patient status system and corresponding to a predetermined location within the healthcare enterprise, a request signal when the wearable identification device is detected at the predetermined location; derive power for the passive sensor from the request signal and not from power circuitry within the wearable device; generate, at the passive sensor using the derived power, a transmission from the request signal, wherein the transmission includes identifying information associated with the wristband; and transmit, from the passive sensor, the transmission to the receiver, wherein the transmission is utilized to update a status of the patient within the patient status system based upon detection of the passive sensor at the predetermined location.

A further aspect provides a product, including: a computer-readable storage device that stores executable code that, when executed by a processor, causes the product to: receive, at a passive sensor of a wearable identification device associated with a patient within a healthcare enterprise from a receiver of a patient status system and corresponding to a predetermined location within the healthcare enterprise, a request signal when the wearable identification device is detected at the predetermined location; derive power for the passive sensor from the request signal and not from power circuitry within the wearable device; generate, at the passive sensor using the derived power, a transmission from the request signal, wherein the transmission includes identifying information associated with the wristband; and transmit, from the passive sensor, the transmission to the receiver, wherein the transmission is utilized to update a status of the patient within the patient status system based upon detection of the passive sensor at the predetermined location.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
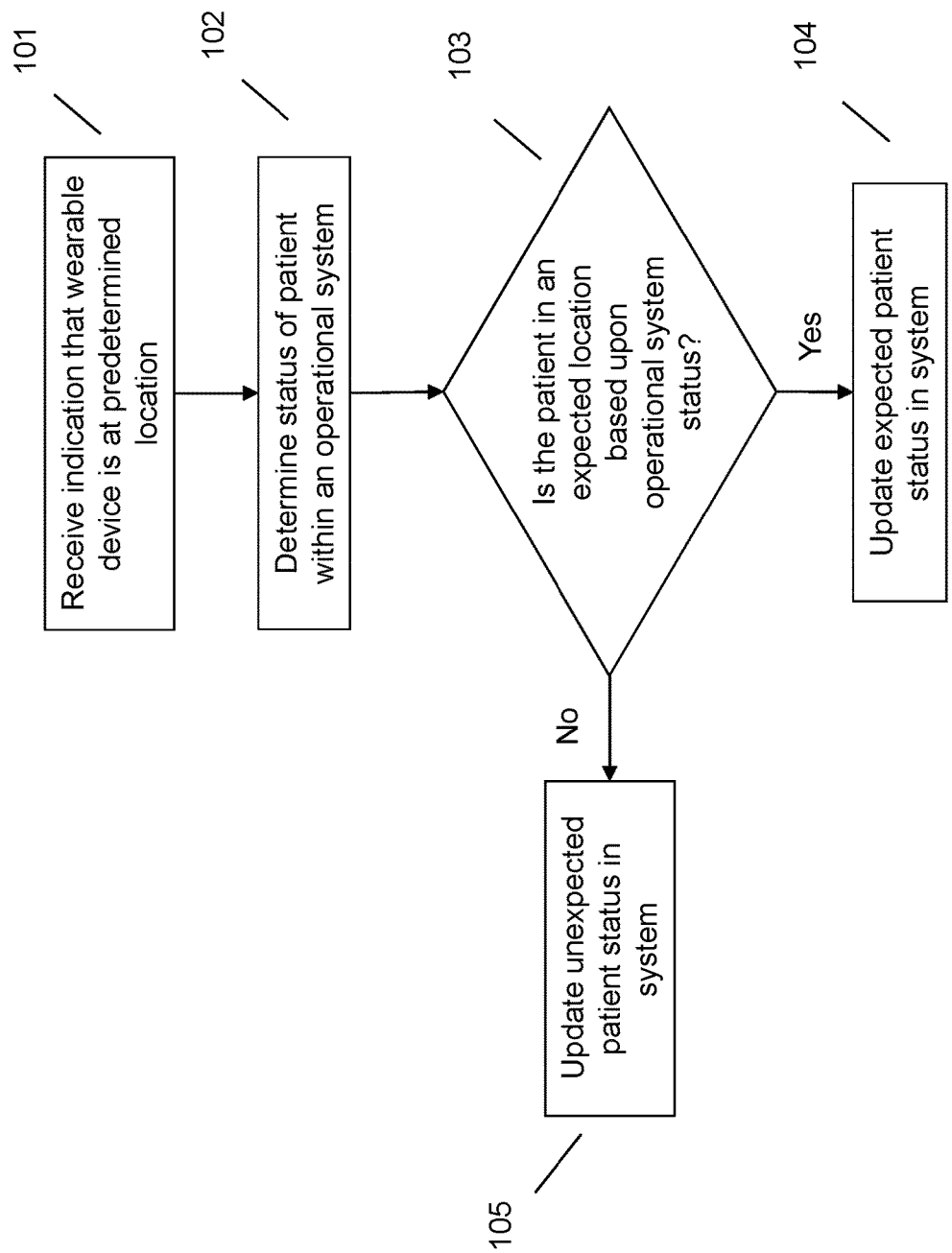
FIG. 1 illustrates an example method of patient identification using passive sensors of a wearable object.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Many hospitals or other businesses may provide wearable identification objects (e.g., lanyards, wristbands, identification cards to be worn by a user, etc.) to each person that enters a building, facility, or other area associated with the hospital or business. These wearable identification objects may provide access to particular areas within the facility. Additionally, these wearable identification objects may allow the business to identify the person wearing the object and, in some cases, may allow the business to identify the location of the person within the facility. For example, many hospital identification wristbands include device circuitry that allows the wristband to communicate with receivers located throughout the facility. As a person or patient travels throughout the hospital or facility, the wristband communicates with these receivers. Based upon which receiver has communicated with the wristband, hospital personnel can be apprised of where the person is within the hospital. Specifically, the transmitters on the wristband will respond to the receiver with a unique identification number which is assigned to each wristband. Thus, upon receipt of the unique identification number the number can be used to identify the wristband and the patient assigned to that wristband. The healthcare enterprise may then update the location of the patient within a system.

For simplicity, the term "hospital" may be used here throughout. However, it should be understood by one skilled in the art that this term may refer to any healthcare enterprise, for example, long-term care facility, emergency department, healthcare staffing area, and the like. Additionally, healthcare enterprise is intended to describe an entire enterprise under a single healthcare provider. In other words, a healthcare enterprise may include one or more buildings that may be located in one or more buildings in one or more geographical areas. Each of the departments within the healthcare enterprise may be referred to herein as a "facility". For example, the emergency department may be one facility, the long-term care department may be another facility, the in-patient department may be another facility, and the like. Each of the facilities may be located in separate buildings or may be located within the same building. For example, an emergency department may be located within the same building as an in-patient care facility.

Hospitals can use the information provided by the identification object to determine when a patient has left the hospital or when hospital personnel should be scheduled to perform various procedures. For example, if the receiver that reads the wristband is a receiver located at the exit of the hospital, systems within the hospital can be updated to designate that the patient has been discharged and is no longer at the hospital. The hospital can then prepare the room previously occupied by that patient for a new patient. As another example, if the receiver that reads the wristband is a receiver located at a door frame of an x-ray room, the hospital system can be updated so that the patient is not scheduled for another procedure at the same time that the patient is getting an x-ray taken. With the use of the identification wristbands, these systems may be updated automatically without needing hospital personnel to update the status of the patient. Additionally, any personnel that need to be notified of the change can be notified automatically. Such a system provides a quicker transition between patients. Additionally, such a system reduces the chances of a patient from being scheduled for multiple procedures at the same time, thereby providing for a more efficient scheduling of both the patient and hospital personnel.

Conventionally the identification objects include active sensor technology, for example, radio frequency identification (RFID) technology. The active sensor technology requires that both the receiver and the identification object include circuitry to power the sensors in each of receiver and the identification object. Accordingly, the identification object (referred to herein as a wristband) may be expensive as compared to other wristbands, for example, paper wristbands without circuitry, and the like. Thus, when the patient leaves the hospital, the hospital requests that the patient return the wristband so that it can be reused. To facilitate this retrieval the hospital either requires that hospital staff remove the wristband or include a dropbox for the patient to return the wristband. Since the patient has to return the wristband and the wristband already includes technology that allows the hospital to identify (e.g., determine) the location of the wristband, the dropbox may be equipped with sensors that detect the wristband when it is placed in the dropbox. Thus, the dropbox may be configured as a discharge location. When the wristband is placed in the dropbox, the sensors of the dropbox detect the wristband and update the hospital's system to indicate that the patient has been discharged. If other factors have been met, as discussed in more detail below, the system updates the status of the patient as confirmed discharge, updates additional systems based upon the discharge status (e.g., the bed status to needing clean, etc.), and sends notification to any pertinent personnel (e.g., housekeeping that the bed needs cleaned, etc.).

One problem with this system is that because the wristband needs to be returned to the hospital, the discharge location needs to be a location where the wristband can be returned. Thus, in the case where a patient forgets or chooses not to return the wristband, the system cannot be updated accordingly. Additionally, if a patient removes the wristband but does not leave the hospital, the system is unaware of where the patient is actually located within the facility. Additionally, if a patient is being transferred between facilities within the healthcare enterprise, the wristband of the patient needs to be removed before leaving one facility and a new wristband needs to be attached to the patient when arriving at the new facility.

Accordingly, an embodiment provides a method for using a wearable object having passive sensor technology to update the status of a patient within a system. The wearable object, or wristband, includes passive sensor technology that does not require circuitry to power the sensor of the wristband. Instead, sensors using passive sensor technology derive the power needed to power the sensor from the signal received from a reader or receiver. An example wristband having passive technology is described in commonly owned U.S. patent application Ser. No. 15/697,781 entitled "ENHANCED IDENTIFICATION WRISTBAND" filed on Sep. 7, 2017, the contents of which are incorporated by reference herein. Using the passive sensor wristband, the hospital can configure different locations as discharge locations, not just a dropbox. Accordingly, when the system receives an indication that the wristband is at a discharge location, the system may update the status of the patient as discharged. Additionally, using the passive technology, other locations within the enterprise can be configured as gateways. Gateways are locations within the healthcare enterprise that identify a transition between one location and another location. For example, a doorway between an emergency department and an in-patient care facility may be configured as a gateway.

The system may then determine the status of the patient within an operational system. This is used to determine where the patient should be. For example, the operational system may indicate that the patient has been discharged by way of inclusion of a physician order indicating that the patient has been discharged or treatment has been completed. As another example, the operational system may indicate that the patient is being transferred between facilities of the healthcare enterprise. Thus, the status of the patient within the operational system may be "transferring". Once the status of the patient has been determined and the wristband has been detected at a predetermined location, the system may be updated with the location of the patient. Depending on if the patient is at an expected or an unexpected location, updating the status of the patient within the system may cause different actions.

The illustrated example embodiments will be best understood by reference to the figures. The following description is intended only by way of example, and simply illustrates certain example embodiments.

Referring now to FIG. 1, at 101, the system may receive an indication that a wearable device comprising a passive sensor is at a predetermined location within a healthcare enterprise. The wristband having passive sensor technology does not include circuitry that powers the sensor within the wristband. Rather, the sensor of the wristband is powered by the receiver or reader that communicates with the wristband. In other words, the wristband sensor derives power from the signal sent by the reader or receiver when the wristband is detected in the vicinity of the reader or receiver. Thus, the cost of the passive wristband is reduced as compared to an active wristband. Therefore, the passive wristbands do not need to be returned to the hospital and can be taken by the patient as the patient leaves the hospital.

To detect that the wristband is a predetermined location, the hospital includes readers or receivers that are located at locations within the hospital. The readers or receivers are stationary. Therefore, each of the readers or receivers has an associated location within the hospital. The locations of the readers may be assigned as a particular type of locations, for example, a discharge location, a gateway location, a transport location, and the like. In other words, the associated location of the reader may be configured by a user within the system to be a particular type of location that results in a particular action taken by a system of the hospital. The locations may include points-of-entry, for example, doorways, or may include entire rooms. For example, a waiting room may be configured as a discharge location. Thus, if the wristband is detected anywhere within the room the system identifies the wristband as being at the predetermined location.

A discharge location may be a location within the hospital that is indicative of the patient leaving the hospital, for example, an exit of the hospital. Thus, when the patient is detected at this location, the system may identify that the patient is leaving the hospital. A gateway location may be a location that indicates a transition from one location to another location. For example, a gateway location may identify that a patient has moved into a particular type of room (e.g., operating room, waiting room, ultrasound room, etc.). As another example, a gateway location may indicate a transition between two facilities (e.g., from emergency department to in-patient care, from in-patient care to long-term care, etc.). A transport location may include an ambulance, helicopter, or other transport vehicle. Additionally, a single location may be configured as two different locations, for example, a discharge location and a gateway location. As an example, an exit of the hospital may be both a discharge location and a gateway location. The system may determine how the location may be treated based upon a status of the patient within an operational system, as discussed in more detail below, for example, with reference to 102.

When a wristband is in proximity to the reader or receiver the reader sends a request signal to the wristband sensor. The request signal requests the identifying information associated with the wristband, for example, an identification number, serial number of the wristband, and the like. As stated before, the passive sensor of the wristband derives enough power from the request signal to provide a return signal including the identifying information to the reader. When the reader receives the return signal, the reader can either process the return signal at the reader or send the information included in the return signal to another system. Each wristband is associated with a patient within a system of the hospital. In other words, the identifying information of the wristband is correlated to a particular patient within the system. Thus, when the return signal including the identifying information is processed, the system can determine which patient was detected at the location of the reader by correlating the identifying information to the patient who was associated with that wristband.

At 102 the system may determine a status of the patient within an operational system associated with the hospital. As the patient is treated within the hospital, the patient care and status is updated within an operational system. A staff member can then access the operational system to determine what treatment the patient has already received, what tests are being performed, and the like. Accordingly, within the operational system, the patient has an associated status (e.g., in treatment, waiting, discharged, transferred, etc.). This status is updated by the staff treating or otherwise interacting with the patient, for example, the nurses, doctors, technicians, and the like. When the status of the patient is updated in the operational system, the patient may not have physically transitioned to that status. As an example, if a doctor has determined that the hospital is done treating the patient, the doctor may put in a discharge order, thereby resulting in a discharge status of the patient. However, the patient may still physically be in the hospital. As another example, the status of the patient in the operational system may be transferred because the patient is being transferred from one facility to another within the hospital. However, the patient may still be in the first facility waiting to be physically transferred from one facility to another.

At 103, the system may identify if the detected location of the patient is an expected location based upon the status of the patient within the operational system. For example, if the patient is detected at a discharge location, and the status of the patient within the operational system is discharged, the location may be determined to be an expected location. If, however, the status of the patient within the operational system is not discharged, the discharge location is an unexpected location of the patient. As another example, if the patient status within the operational system is transferred, the patient being detected at a gateway location or transport location is expected, while the patient being detected at a discharge location is unexpected. Thus, the status of the patient within the operational system is compared with the detected location of the patient to determine if the patient should have been detected at the predetermined location. In other words, the detected location of the patient is compared to the status of the patient within the operational system to determine if the detected location is an expected or unexpected location.

At either 104 or 105 the system updates the status of the patient within a system of the hospital. At 104 updating the status of the patient within the system is performed in response to the location being an expected location. At 105 updating the status of the patient within the system is performed in response to the location being an unexpected location. Thus, the system updates, based upon the determined status of the patient within the operational system and the detected location, the system of the hospital. Updating the system includes updating the status of the patient within the system. For example, if the patient has been detected at a gateway location (e.g., the patient enters the operating room, the patient enters the waiting room, the patient arrives at a new facility, etc.), updating the status of the patient includes updating the location of the patient within the system. As another example, if the patient is detected at a discharge location and the status of the patient within the operational system is discharged, the location is expected and the system may update the status of the patient as confirmed discharge. If the patient is detected at a discharge location and the status of the patient within the operational system is not discharged, the location is unexpected and the system may update the status of the patient to indicate that the patient has left the hospital without being discharged.

As another example, if the patient is detected at a gateway location associated with another facility and the patient status within the operational system is transferred, the location is expected and the status of the patient is updated to identify that the patient has left one facility and/or arrived at another facility. Similarly, if the patient is detected at a transport location with a patient status of transferred, the location is expected and the status of the patient is updated to reflect that the patient is in the transport location. If, however, the patient is detected at a gateway or transport location without a status of transferred, the location is unexpected, and the status of the patient may be updated to reflect the unexpected location. Updating the status of the patient may include updating a display associated with the system to reflect the new status of the patient.

The system may also take additional action based upon the location being expected or unexpected. For example, if a patient is detected at an unexpected location, the system may provide an alert or notification to hospital personnel indicating the unexpected location. As an example, if the system includes a display, the system may highlight an icon associated with the patient or location, cause an icon associated with the patient or location to blink, provide a pop-up notification, or otherwise provide an indication on the display that brings a user's attention to the unexpected location. Other actions may also occur, for example, doors near the unexpected location may lock, an alarm may sound, or the like.

Based upon updating the status of the patient within the system, additional actions may occur. For example, if a patient status is changed to confirmed discharge, hospital personnel may be notified of the confirmed discharge status. As an example, when a patient is in the hospital, the patient has a room and/or bed associated with the patient. When the patient is discharged, the hospital wants the room to be turned-over quickly so that a new patient can be moved to the room. Thus, once the patient status is identified as confirmed discharge, the system may update a status of the room and/or bed to needing cleaned. The system may additionally send a notification to the environmental services department that the room and/or bed is ready to be cleaned.

Additionally, if the system does not detect the wearable device for a predetermined length of time, the system can perform some action within the system. For example, the system may remove the wristband from the system, the system may provide an alert that the wristband has not been seen, or the system may change the status of a patient associated with the wristband to confirmed discharged.

The various embodiments described herein thus represent a technical improvement to current systems for identifying patients within a healthcare enterprise. Rather than requiring an active wristband that has to be returned to the hospital upon discharge, the systems and techniques herein provide a passive wristband. Using the passive wristband, the system can detect the patient at different locations that are configured as different identified locations (e.g., gateway location, discharge location, transport location, etc.). Thus, when the patient is detected at the location, the system can check the status of the patient in the operational system and update the patient status within a system based upon whether the location is expected or unexpected. Thus, the systems and methods as described herein provide a technique that allows more than just a dropbox to be configured as a discharge location and also provides a method for identifying the patient throughout an entire healthcare enterprise without the user having to get a new wristband at every facility within the healthcare enterprise.

While various other circuits, circuitry or components may be utilized in information handling devices, with a computer, server, client device or the like, an example device that may be used in implementing one or more embodiments includes a computing device in the form of a computer 200. This example device may be a server used in one of the systems in a hospital network, or one of the remote computers connected to the hospital network. Components of computer 200 may include, but are not limited to, a processing unit 220, a system memory 230, and a system bus 222 that couples various system components including the system memory 230 to the processing unit 220. Computer 200 may include or have access to a variety of computer readable media, including databases. The system memory 230 may include non-signal computer readable storage media, for example in the form of volatile and/or nonvolatile memory such as read only memory (ROM) and/or random access memory (RAM). By way of example, and not limitation, system memory 230 may also include an operating system, application programs, other program modules, and program data.

A user can interface with (for example, enter commands and information) the computer 200 through input devices 250. A monitor or other type of device can also be connected to the system bus 222 via an interface, such as an output interface 260. The computer may include a database 240. In addition to a monitor, computers may also include other peripheral output devices. The computer 200 may operate in a networked or distributed environment using logical connections to one or more other remote device(s) 280 such as other computers. The logical connections may include network interface(s) 270 to a network, such as a local area network (LAN), a wide area network (WAN), and/or a global computer network, but may also include other networks/buses.

Figure 2:
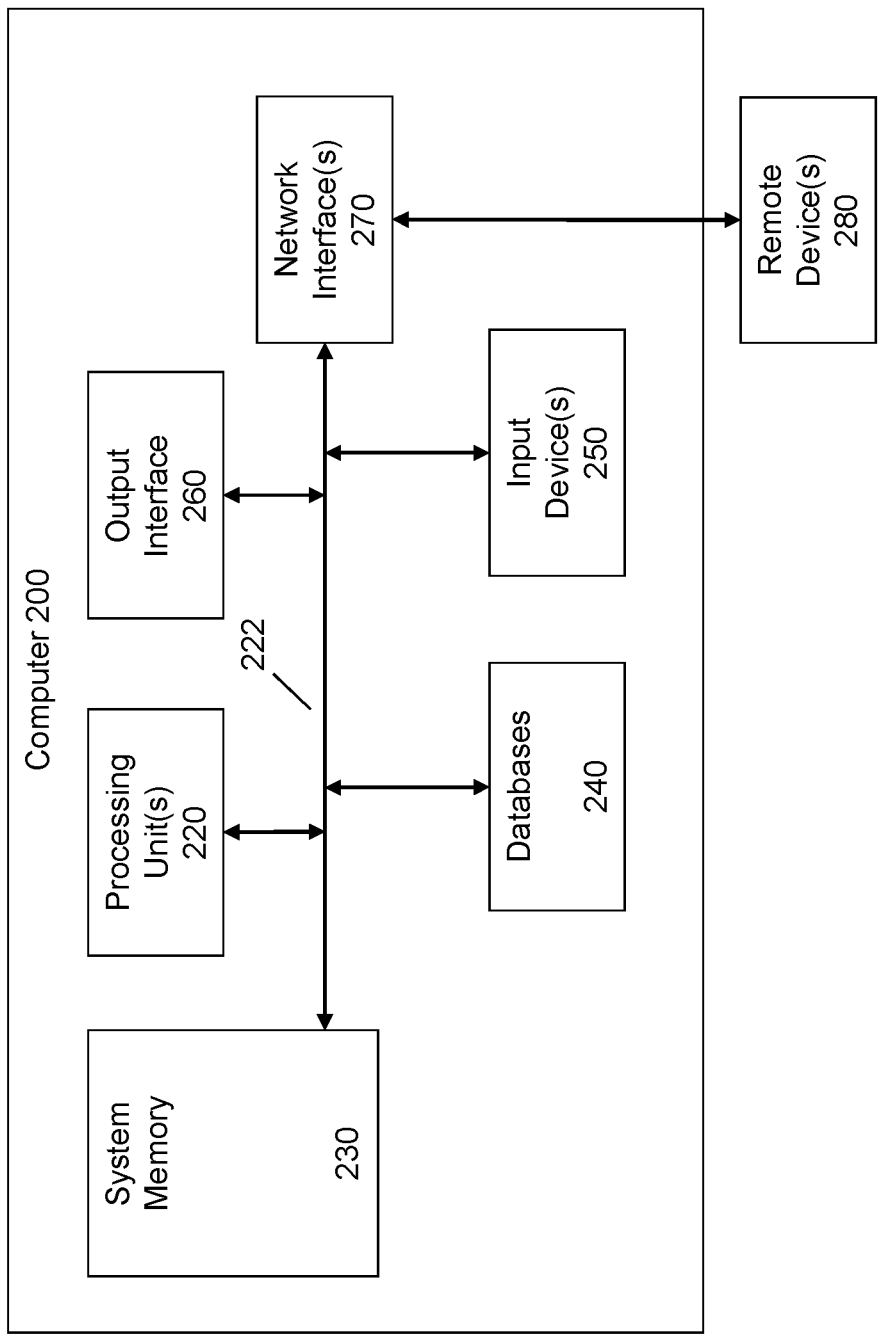
FIG. 2 illustrates an example of device circuitry.

Information handling device circuitry, as for example outlined in FIG. 2, may be used in client devices such as a personal desktop computer, a laptop computer, or smaller devices such as a tablet or a smart phone. In the latter cases, i.e., for a tablet computer and a smart phone, the circuitry outlined in FIG. 2 may be adapted to a system on chip type circuitry. The device, irrespective of the circuitry provided, may provide and receive data to/from another device, e.g., a server or system that coordinates with various other systems. As will be appreciated by one having ordinary skill in the art, other circuitry or additional circuitry from that outlined in the example of FIG. 2 may be employed in various electronic devices that are used in whole or in part to implement the systems, methods and products of the various embodiments described herein.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method comprising:
receiving, at a passive sensor of a wearable identification device associated with a patient within a healthcare enterprise, a request signal transmitted by a receiver of a patient status system located at a predetermined location within the healthcare enterprise, wherein the request signal is received by the passive sensor when the wearable identification device is detected at the predetermined location;
deriving, by the passive sensor, power for the passive sensor from the request signal and not from power circuitry within the wearable device;
generating, by the passive sensor using the derived power, a transmission responsive to the request signal, wherein the transmission comprises identifying information associated with the wristband; and
transmitting, from the passive sensor, the transmission to the receiver, wherein the transmission is utilized to update a status of the patient within the patient status system based upon detection of the passive sensor at the predetermined location.

2. The method of claim 1, wherein to update the status of the patient comprises updating a display of the patient status system based upon the updated status of the patient and notifying at least one user of the updated status of the patient.

3. The method of claim 1, wherein the predetermined location comprises at least one of a discharge location and a location gateway.

4. The method of claim 1, wherein to update a status of the patient is responsive to determining, by accessing an operational system of the healthcare enterprise using the patient status system, a healthcare treatment status of the patient within the operational system.

5. The method of claim 4, wherein to update a status of the patient is further responsive to determining, using the patient status system, whether the patient is in an expected location at the predetermined location based upon the healthcare treatment status of the patient.

6. The method of claim 5, wherein the determining whether the patient is in an expected location comprises comparing the predetermined location to a location associated with the healthcare treatment status.

7. The method of claim 4, wherein the determining a healthcare treatment status of the patient comprises determining if a discharge order exists for the patient within the operational system.

8. The method of claim 1, wherein the identifying information comprises at least one of: an identification number of the wristband and a serial number of the wristband.

9. The method of claim 1, wherein the wearable identification device is associated with a patient within a healthcare enterprise via the identifying information corresponding to a particular patient within the healthcare enterprise.

10. The method of claim 1, further comprising determining if the wearable device meets a predetermined condition, wherein the predetermined condition comprises a predetermined time period elapsing since a last received indication from the wearable device.

11. An information handling device, comprising:
a processor;
a memory device that stores instructions that, when executed by the processor, causes the information handling device to:
receive, at a passive sensor of a wearable identification device associated with a patient within a healthcare enterprise, a request signal transmitted by a receiver of a patient status system located at a predetermined location within the healthcare enterprise, wherein the request signal is received by the passive sensor when the wearable identification device is detected at the predetermined location;
derive, by the passive sensor, power for the passive sensor from the request signal and not from power circuitry within the wearable device;
generate, by the passive sensor using the derived power, a transmission responsive to the request signal, wherein the transmission comprises identifying information associated with the wristband; and
transmit, from the passive sensor, the transmission to the receiver, wherein the transmission is utilized to update a status of the patient within the patient status system based upon detection of the passive sensor at the predetermined location.

12. The information handling device of claim 11, wherein to update the status of the patient comprises updating a display of the patient status system based upon the updated status of the patient and notifying at least one user of the updated status of the patient.

13. The information handling device of claim 11, wherein the predetermined location comprises at least one of a discharge location and a location gateway.

14. The information handling device of claim 11, wherein to update a status of the patient is responsive to determining, by accessing an operational system of the healthcare enterprise using the patient status system, a healthcare treatment status of the patient within the operational system.

15. The information handling device of claim 14, wherein to update a status of the patient is further responsive to determining, using the patient status system, whether the patient is in an expected location at the predetermined location based upon the healthcare treatment status of the patient.

16. The information handling device of claim 15, wherein the determining whether the patient is in an expected location comprises comparing the predetermined location to a location associated with the healthcare treatment status.

17. The information handling device of claim 4, wherein the determining a healthcare treatment status of the patient comprises determining if a discharge order exists for the patient within the operational system.

18. The information handling device of claim 11, wherein the identifying information comprises at least one of: an identification number of the wristband and a serial number of the wristband.

19. The information handling device of claim 11, wherein the wearable identification device is associated with a patient within a healthcare enterprise via the identifying information corresponding to a particular patient within the healthcare enterprise.

20. A product, comprising:
a non-transitory computer-readable storage device that stores executable code that, when executed by a processor, causes the product to:
receive, at a passive sensor of a wearable identification device associated with a patient within a healthcare enterprise, a request signal transmitted by a receiver of a patient status system located at a predetermined location within the healthcare enterprise, wherein the request signal is received by the passive sensor when the wearable identification device is detected at the predetermined location;
derive, by the passive sensor, power for the passive sensor from the request signal and not from power circuitry within the wearable device;
generate, by the passive sensor using the derived power, a transmission responsive to the request signal, wherein the transmission comprises identifying information associated with the wristband; and
transmit, from the passive sensor, the transmission to the receiver, wherein the transmission is utilized to update a status of the patient within the patient status system based upon detection of the passive sensor at the predetermined location.

* * * * *